United States Patent [19]

Goux et al.

[11] Patent Number: 5,399,157
[45] Date of Patent: Mar. 21, 1995

[54] METHOD FOR CHECKING THE OPERATION OF SENSORS SITUATED IN A DIALYSIS LIQUID CIRCUIT

[75] Inventors: Nicolas Goux, Tassin la Demi Lune; Bernard Bene, Irigny, both of France

[73] Assignee: Hospal Industrie, France

[21] Appl. No.: 85,932

[22] Filed: Jul. 6, 1993

[30] Foreign Application Priority Data

Jul. 6, 1992 [FR] France .................. 92 08564

[51] Int. Cl.⁶ ............................................. A61M 37/00
[52] U.S. Cl. ..................................... 604/4; 604/5; 128/692; 324/439; 324/555
[58] Field of Search ............... 604/4, 5, 8, 9, 29, 604/52, 93, 175, 236, 256; 324/439, 555; 128/691, 692

[56] References Cited

U.S. PATENT DOCUMENTS

| | | |
|---|---|---|
| 4,153,554 | 5/1979 | von der Heide et al. |
| 4,209,391 | 6/1980 | Lipps et al. |
| 4,508,622 | 4/1985 | Polaschegg et al. |
| 4,683,053 | 7/1987 | Polaschegg |
| 4,736,748 | 4/1988 | Nakamura et al. ............ 604/4 |
| 4,897,184 | 1/1990 | Shouldice et al. |
| 4,923,598 | 5/1990 | Schäl ............................ 604/5 |
| 4,966,691 | 10/1990 | Brous |
| 4,967,754 | 11/1990 | Rossi ............................ 604/5 |
| 5,004,548 | 4/1991 | Richalley et al. ............. 604/5 |
| 5,024,756 | 6/1991 | Sternby |
| 5,091,094 | 2/1992 | Veech |
| 5,100,554 | 3/1992 | Polaschegg |
| 5,171,212 | 12/1992 | Buck et al. .................... 604/4 |
| 5,195,963 | 3/1993 | Yafuso et al. ................ 128/692 |
| 5,211,849 | 5/1993 | Kitaevich et al. ............. 604/4 |

FOREIGN PATENT DOCUMENTS

| | | |
|---|---|---|
| 0097366 | 1/1984 | European Pat. Off. |
| 0330892 | 6/1989 | European Pat. Off. |
| 0428997 | 5/1991 | European Pat. Off. |
| 3436748 | 4/1985 | Germany |

OTHER PUBLICATIONS

"Optimization of Sodium Dialysate Concentration by Plasma Water Conductivity Monitoring," T. Petitclerc et al., Progress in Artificial Organs–1985, ISAO Press, Cleveland 1986, pp. 234–236.

Primary Examiner—Paul Prebilic
Attorney, Agent, or Firm—Finnegan, Henderson, Farabow, Garrett & Dunner

[57] ABSTRACT

The invention is a method for checking the operation of at least one sensor situated in a dialysis liquid circuit of an artificial kidney. The method includes causing a reference liquid of known characteristics to circulate in the extracorporeal blood circuit, taking a measurement to check at least one characteristic of the dialysis liquid by means of the sensor, calculating the theoretical value of at least one characteristic of the reference liquid on the basis of the measurement, comparing the calculated theoretical value with the known value of the said characteristic of the reference liquid, concluding that the sensor is working properly after the measurement has been taken when the calculated theoretical value is substantially equal to the known value. A device for the application of this method is also disclosed.

21 Claims, 2 Drawing Sheets 4,399,157

METHOD FOR CHECKING THE OPERATION OF SENSORS SITUATED IN A DIALYSIS LIQUID CIRCUIT

BACKGROUND OF THE INVENTION

1. Field of the Invention

The present invention concerns extracorporeal treatment of blood by dialysis. More particularly, the present invention is directed to a method for checking the operation of sensors situated in a dialysis liquid circuit of an artificial kidney.

2. Description of the Related Act

In a dialysis liquid circuit of an artificial kidney there are many sensors making it possible to measure or check a certain number of characteristics of the dialysis liquid, such, as for example, the conductivity or concentration of salts. Such characteristics are useful to know and to monitor in the course of a treatment session since the efficiency of the blood purification depends on the composition of the dialysis liquid used. In addition, it is possible in certain cases to deduce the value of certain characteristics of the blood by means of measurements carried out on the dialysis liquid.

In particular, one may determine the concentration of sodium in the blood circulating on the other side of a membrane based on measurements of the conductivity of the dialysis liquid, which avoids the need for taking blood samples from the patient. The measurement of the conductivity may be carried out by recirculating dialysis liquid in a part of the blood circuit, until an equilibrium with the blood is obtained, as described in the article "Optimization of Sodium Concentration by Plasma Water Conductivity Monitoring" by Petitclerc, Man, Goureau, Jehenne and Funck-Brentano (Progress in Artificial Organs—1985). Alternatively and more advantageously, conductivity may be measured by means of two measurements effected respectively upstream and downstream from the device used for the blood treatment. The two measurements may even be obtained, if required, by means of a single conductivity meter alternately washed by the fresh dialysis liquid and by the used dialysis liquid. The natraemia determinations thus effected may subsequently be used to determine the composition of the most favorable dialysis liquid according to the purification desired. Hence, it is very important that the data provided by the conductivity meter are reliable. The conventional means for checking the operation of the conductivity meters usually necessitates a considerable period of downtime for the artificial kidney, which reduces the time available for patient treatment.

SUMMARY OF THE INVENTION

An object of the invention is to remedy the drawbacks of the prior art and to propose a method to check the operation of sensors present in a dialysis liquid circuit without entailing downtime of the dialysis apparatus.

To attain the objects of the invention, the present invention is a method for checking the functioning of at least one sensor situated in a dialysis liquid circuit of an artificial kidney comprising an exchanger with two compartments separated by a semipermeable membrane, one of the compartments being connected to the dialysis liquid circuit, while the other compartment is connected to an extracorporeal blood circuit. The method comprises causing a reference liquid of known characteristics to circulate in the extracorporeal blood circuit, taking a measurement of at least one characteristic of the dialysis liquid by means of at least one sensor, calculating the theoretical value of at least one characteristic of the reference liquid on the basis of the measurement, comparing the calculated theoretical value with the known value of the characteristic of the reference liquid, and concluding, after the measurement has been taken, that the sensor is functioning properly when the calculated theoretical value is substantially equal to the known value.

Preferably, the reference liquid is a sterile solution of a physiological serum. Thus, the characteristics of this solution are thoroughly known and may be used to check the accuracy of the measurement means situated in the dialysis liquid circuit.

According to another aspect of the invention, the checking procedure preferably is operated during the stage of rinsing and priming of the haemodialyzer. It is thus possible, without introducing a supplementary stage, to check the proper functioning of the sensors at the beginning of each treatment session.

Another object of the invention is a device for operating the method according to the invention. The device comprises means for causing a reference liquid of known characteristics to circulate in the extracorporeal blood circuit, at least one sensor for measuring at least one characteristic of the dialysis liquid, and computing means for determining the theoretical value of at least one characteristic of the reference liquid on the basis of at least one measurement taken on the dialysis liquid, and for comparing the calculated theoretical value with the known value of the said characteristic of the reference liquid.

Other features and advantages of the present invention will emerge on reading the description that follows with reference to the diagrams in which only the elements necessary for understanding the present invention are shown.

DETAILED DESCRIPTION OF THE PREFERRED EMBODIMENT

Figure 1:
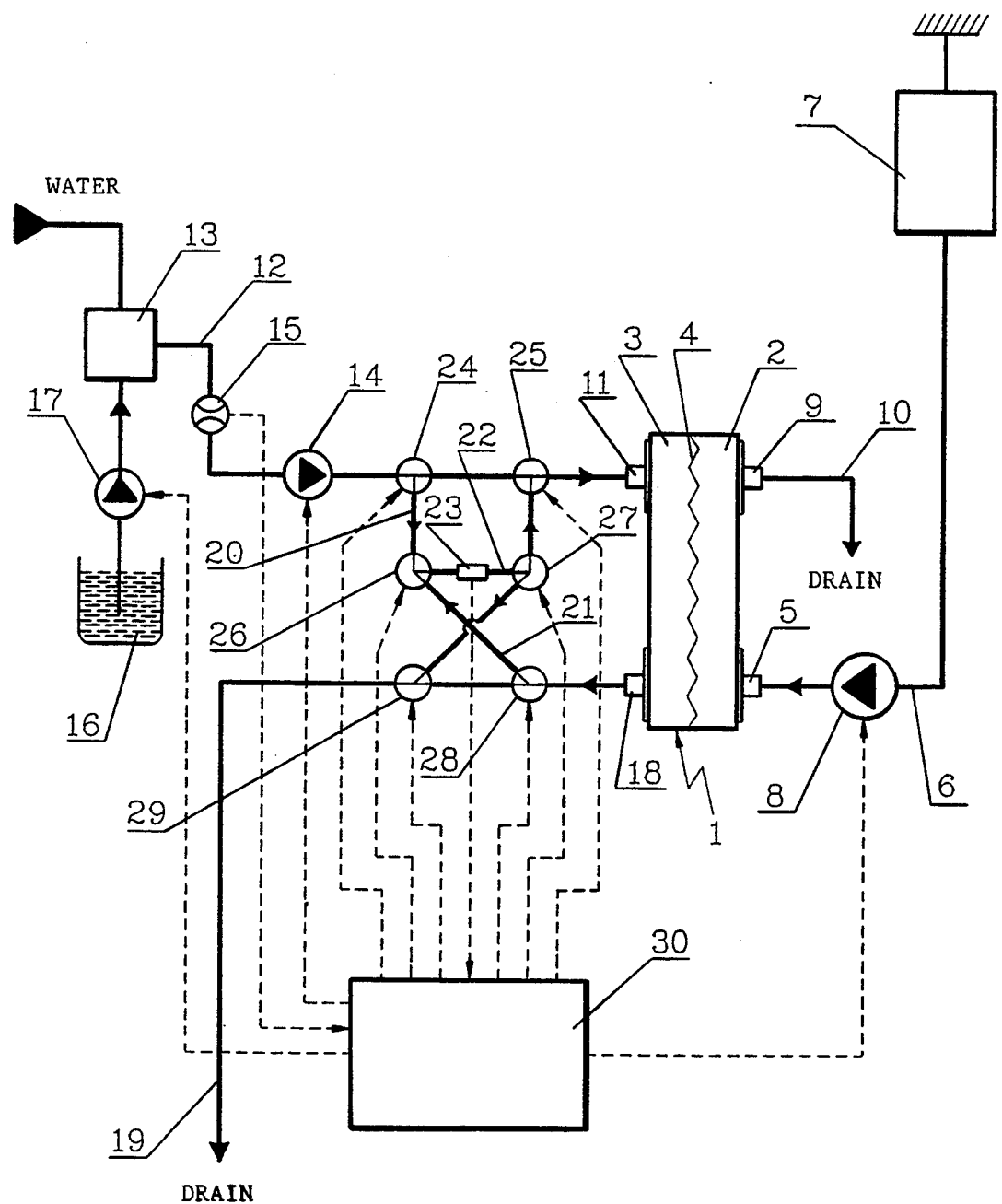
FIG. 1 illustrates a first embodiment of the present invention.

An artificial kidney, illustrated in FIG. 1, includes a haemodialyzer 1 having two compartments 2, 3 separated by a semi-permeable membrane 4 permitting the dialysis of the blood. The compartment 2 is for the circulation of blood to be treated, while the compartment 3 is for the circulation of dialysis liquid.

During a checking operation, illustrated in FIG. 1, an intake 5 of the compartment 2 is connected by a line 6 to a source 7 of a reference liquid, whose composition is completely determinate. A pump 8 ensures the circulation of the reference liquid. The outlet 9 of the compartment 2 is connected by a line 10 to the drain.

The compartment 3 of the haemodialyzer has an intake 11 connected via a feeding line 12 to a source 13 of dialysis liquid. The line 12 comprises a flowmeter 15 and a pump 14 which ensures the circulation of the dialysis liquid.

The source 13 of dialysis liquid is fed with water and with a concentrated solution present in a reservoir 16.

The feeding rate of the source 13 with the concentrated solution is regulated by a pump 17. The outlet 18 of the compartment 3 is connected to a line 19 for discharging the used dialysis liquid to the drain.

The feeding line 12 and the discharge line 19 each have a bypass circuit, 20 and 21, respectively. These two bypass circuits include a common portion 22 equipped with a sensor 23 constituted, for example, by an electrode specific to sodium.

An appropriate set of valves 24, 25, 26, 27, 28, 29 makes it possible to selectively connect the common portion 22 equipped with the sensor 23 to the fresh dialysis liquid supply line 12 or to the line 19 for the evacuation of the used dialysis liquid.

A control unit 30 receives data coming from the flowmeter 15 and from the sensor 23. Unit 30 controls the positioning of the valves 24, 25, 26, 27, 28 and 29, as well as the operation of the pumps 8, 14, and 17.

Prior to the operation of the artificial kidney, the operator supplies data to the unit 30 concerning the characteristics of the haemodialyzer used, as well as instructions relating to the delivery rate of the pump 8, the delivery rate of the pump 14, and to the desired conductivity of the dialysis liquid.

The operation of the artificial kidney is as follows. The reference liquid 7 is put into circulation by means of the action of the pump 8. This liquid 7 passes into the haemodialyzer via the intake 5, to emerge therefrom via the outlet 9, before being discharged to the drain. Advantageously, the reference liquid used may be the sterile physiological serum solution used for rinsing and filling the circuit for the extracorporeal circulation of the blood to be treated.

During this time, the unit 30 controls the operation of the pump 17 in accordance with the conductivity set point established by the operator. The concentrate is diluted by means of the water feeding the source 13. After being heated by means of an appropriate device (not shown), the dialysis liquid thus prepared is caused to circulate by means of the pump 14. The operation of this pump is controlled by the unit 30 in response to the flow rate values which are transmitted to it by the flowmeter 15. The dialysis liquid passes into the compartment 3 of the haemodialyzer via the intake 11, then emerges therefrom via the outlet 18 before being passed to the drain by means of the line 19. Inside the haemodialyzer, exchanges take place between the two liquids by dialysis through the membrane 4, where the liquid with a high concentration of a certain substance becomes more diluted as the liquid with the lower concentration becomes stronger.

The quantity of the substance transferred through the membrane is represented by the dialysance, which is a characteristic specific to each membrane. The formula for obtaining the dialysance is as follows:

$$D = \frac{Qd(C_{ind} - C_{outd})}{C_{ind} - C_{inb}} \quad (1)$$

In this formula:
Qd is the flow rate of the dialysis liquid measured by the flowmeter 15
$C_{ind}$ is the concentration of a substance at the intake of the compartment 3 of the haemodialyzer
$C_{outd}$ is the concentration of the same substance at the outlet of the compartment 3 of the haemodialyzer
$C_{inb}$ is the concentration of the same substance at the intake of the compartment 2 of the haemodialyzer.

When the concentration of the dialysis liquid is caused to vary at the intake from $C_{ind1}$ to $C_{ind2}$, a variation of the concentration is obtained at the outlet which passes from $C_{outd1}$ to $C_{outd2}$.

The application of this formula for obtaining the dialysance at these two concentrations leads to the following equation:

$$D = \frac{Qd(C_{ind} - C_{outd})}{C_{ind1} - C_{inb}} = \frac{Qd(C_{ind2} - C_{outd2})}{C_{ind2} - C_{inb}} \quad (2)$$

Since the flow rate of the dialysis liquid Qd is kept constant, one may deduce therefrom the concentration of the liquid circulating in the compartment 2 of the haemodialyzer:

$$C_{inb} = \frac{(C_{outd1} \times C_{ind2}) - (C_{outd2} \times C_{ind1})}{(C_{out1} - C_{ind1}) + (C_{ind2} - C_{outd2})} \quad (3)$$

When the value of $C_{inb}$ is replaced in either term of the equation (2) by the formula obtained in (3), the following formula is obtained for the dialysance D:

$$D = Qd \frac{(1 - C_{outd1} - C_{outd2})}{(C_{ind1} - C_{ind2})} \quad (4)$$

In accordance with the invention, the liquid circulating in the compartment 2 is a reference liquid whose composition is thoroughly known; therefore, the theoretical value of $C_{inb}$ is known.

Thus, in order to check the proper functioning of the sensor 23, the control unit 30 varies the dialysis liquid concentration in accordance with a preestablished program, by varying the speed of the pump 17. First, the positioning of the valves 24, 25, 26, 27, 28 and 29 is controlled by control unit 30 in such a way that the fresh dialysis liquid makes use of the bypass circuit 20, and hence washes the sensor 23 before passing into the haemodialyzer, while the used dialysis liquid circulates directly towards the drain without using the bypass circuit 21. The result of the measurement obtained by the sensor 23 is transmitted to the unit 30 which records it as $C_{ind1}$. When the measurement has been taken, the unit 30 sends a signal to change positions of the valves 24, 25, 26, 27, 28 and 29, so that the fresh dialysis liquid follows the main line 12 to pass directly into the haemodialyzer, and so that the used dialysis liquid uses the bypass circuit 21 to wash the sensor 23. The result of this measurement is then transmitted to the unit 30 which records it as $C_{outd1}$.

The unit 30 then changes the instruction for operating the pump 17, so as to change the composition of the dialysis liquid. The positioning of the valves are reversed so that the common portion 22 is again in communication with the line 12. The measurement carried out by the sensor 23 is transmitted to the unit 30 which records it as $C_{ind2}$.

Then the unit 30 again reverses the positioning of the valves, so that the sensor 23 is able to measure the concentration of the used dialysis liquid. The result of the measurement is then transmitted and recorded as $C_{outd2}$.

On the basis of the recorded results, the unit 30 calculates a value for the concentration of the liquid circulating in the compartment 2 by means of the equation (3).

This calculated value is compared with the theoretical value. When the two values coincide, the correct operation of the sensor 23 is confirmed. When this is not the case, provision may be made for setting off an alarm or the emission of a message warning the operator of the faulty operation of the sensor 23.

When the correct operation of the sensor 23 has been confirmed, it is possible to check the performance of the haemodialyzer by calculating by means of the formula (4) the value of the dialysance obtained from the values $C_{ind1}$, $C_{ind2}$, $C_{outd1}$, $C_{outd2}$ transmitted by the sensor 23 and the flow rate value of the dialysis liquid indicated by the flowmeter 15. This calculated value of the dialysance may then be compared with the value indicated by the manufacturer insofar as the conditions of ultrafiltration through the membrane are substantially identical.

The nature of the sensor 23 may vary. It is possible to use a conductivity meter as well as any sensor capable of measuring the concentration of a substance present in the dialysis liquid. In the case where the measurements are effected by two different sensors, one for the fresh dialysis liquid and the other for the used dialysis liquid, the checking is effected for the set constituted by the two sensors, but does not allow the faulty sensor to be isolated in the case of incorrect operation.

Figure 2:
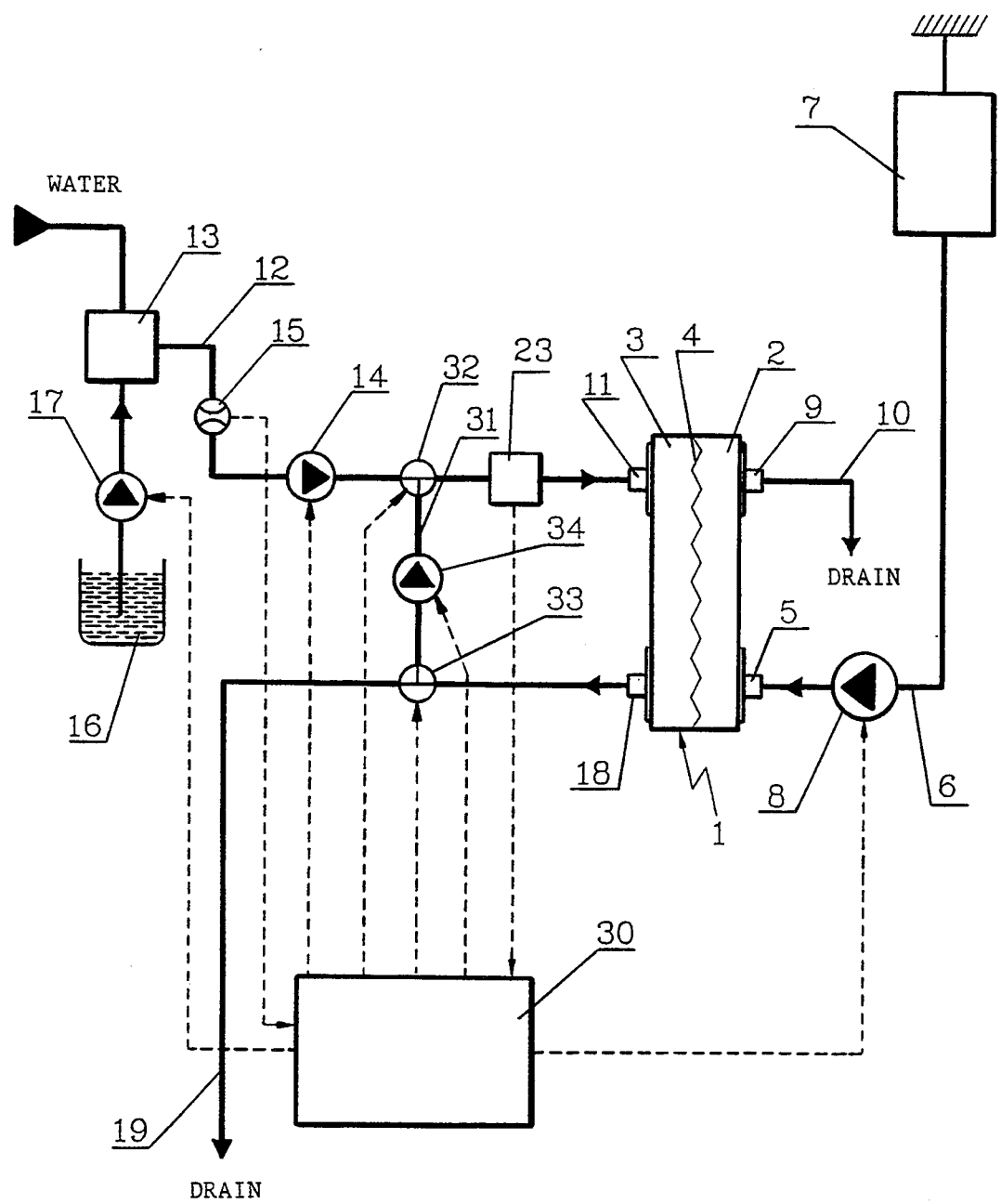
FIG. 2 illustrates a second embodiment of the present invention.

According to the embodiment illustrated in FIG. 2, the dialysis liquid circuit is arranged so as to form a recirculation loop. For this purpose, a line 31 provided with a pump 34 connects the intake line 12 for the fresh dialysis liquid to the line 19 for discharging the used dialysis liquid. The communication of the line 31 with the intake line 12 for the fresh dialysis liquid is obtained by means of a three-way valve 32. Similarly, the communication of the line 31 with the discharge line 19 for the used dialysis liquid is obtained by means of a three-way valve 33. In this configuration, the conductivity meter 23 is situated on the line 12 downstream from the valve 32. The control unit 30 receives data from the conductivity meter 23 and controls the operation of the pump 34 as well as the positioning of the valves 32 and 33.

The operation of the artificial kidney of the second embodiment is as follows. As in the first embodiment, the reference liquid of known conductivity which is present in the reservoir 7, is caused to circulate by means of the pump 8 controlled by the unit 30. Simultaneously, the unit 30 controls the positioning of the valves 32 and 33 so as to permit the circulation of the dialysis liquid directly from the source 13 to the intake 11 of the haemodialyzer, then from the outlet 18 to the drain. The pump 34 does not operate. The starting of the pump 17 is controlled by the unit 30 according to the conductivity set point fixed beforehand by the operator. The unit 30 also controls the functioning of the pump 14 to provide a flow rate of the liquid of 0.5 l/min, which rate is controlled by the flowmeter 15. When the lines 12 and 19 of the dialysis liquid circuit are filled, the unit 30 controls the pump 14 to stop, the pump 34 to start, as well as a change in position of the valves 32 and 33 so as to cause the line 31 to communicate with the line 12 and with the line 19. The dialysis liquid then recirculates in a loop at the flow rate fixed by the pump 34, which rate is at least 0.5 l/min. The measurements taken by the conductivity meter 23 are transmitted to the unit 30. As long as the conductivity value varies, exchanges are taking place by diffusion through the membrane. When the conductivity measured by the conductivity meter 23 no longer changes, the dialysis liquid is in equilibrium with the reference liquid circulating on the other side of the membrane 4. The value then measured is transmitted to the unit 30, which records it as the conductivity at equilibrium. The unit 30 then stops the pump 34, restarts the pump 14, and reverses the position of the valves 32 and 33. This isolates the line 31 and allows the circulation of the dialysis liquid directly from the source 13 to the haemodialyzer 1, then from the haemodialyzer towards the drain without any recirculation.

The unit 30 then checks that the conductivity meter is functioning properly by comparing the recorded conductivity value of the dialysis liquid in equilibrium with the known conductivity value of the reference liquid.

In the same way as in the first embodiment, when the two values coincide, the proper functioning of the conductivity meter 23 is confirmed, while in the opposite case, provision may be made for the setting off of an alarm or for sending a warning message to the operator.

The present invention is not limited to the examples described. Various modifications can be applied thereto without departing from its scope. Thus, it is possible to make provision for the sensor 23 to be recalibrated so as to make the two values coincide, if the calculated value of a characteristic of the reference liquid does not correspond to the theoretical value.

What is claimed is:

1. A method for checking operation of at least one sensor situated in a dialysis liquid circuit of an artificial kidney, the artificial kidney including an exchanger with two compartments separated by a semi-permeable membrane, one compartment being connected to the dialysis liquid circuit while another compartment is intended to be connected to an extracorporeal blood circuit, the method comprising the steps of:
   circulating a noncorporeal reference liquid having a known characteristic value in the extracorporeal blood circuit;
   circulating a dialysis liquid in the dialysis liquid circuit and measuring a first value upstream and downstream from the exchanger;
   varying a composition of the dialysis liquid, and measuring a second value upstream and downstream from the exchanger for the varied composition;
   calculating a characteristic value of the reference liquid on the basis of said first and second values;
   comparing the calculated characteristic value with the known characteristic value of the reference liquid; and
   determining that said sensor is functioning properly when the calculated characteristic value is substantially equal to the known characteristic value.

2. The method according to claim 1, wherein the reference liquid is a sterile solution.

3. A method for checking operation of at least one sensor situated in a dialysis liquid circuit of an artificial kidney, the artificial kidney including an exchanger with two compartments separated by a semi-permeable membrane, one compartment being connected to the dialysis liquid circuit while another compartment is intended to be connected to an extracorporeal blood circuit, the method comprising the steps of:
   circulating a noncorporeal reference liquid having a known characteristic value in the extracorporeal blood circuit;
   circulating a determined quantity of a dialysis liquid inside the exchanger until the dialysis liquid is in equilibrium with the reference liquid for at least one characteristic;

measuring at least one characteristic value of a dialysis liquid by means of at least one sensor;

comparing the measured characteristic value with the known characteristic value of the reference liquid; and determining that said sensor is functioning properly when the measured characteristic value is substantially equal to the known characteristic value.

4. The method according to claim 3, wherein the artificial kidney further comprises means for warning the operator when the calculated characteristic value is not substantially equal to the known characteristic value and wherein the operator is warned by the means for warning.

5. The method according to claim 3, wherein the step of measuring includes measuring a conductivity of the dialysis liquid.

6. The method according to claim 3, wherein the reference liquid is a sterile solution.

7. The method according to claim 3, further comprising beginning the step of circulating a non-corporeal reference liquid when the exchanger is in a rinsing and priming stage.

8. The method according to claim 1, wherein the artificial kidney further comprises means for warning the operator when the calculated characteristic value is not substantially equal to the known characteristic value and wherein the operator is warned by the means for warning.

9. The method according to claim 1, further comprising circulating the dialysis liquid inside the exchanger until the dialysis liquid is in equilibrium with the reference liquid, and performing said measuring step when the equilibrium is reached.

10. The method according to claim 8, further comprising circulating the dialysis liquid inside the exchanger until the dialysis liquid is in equilibrium with the reference liquid, and performing said measuring step when the equilibrium is reached.

11. The method according to claim 1, further comprising varying a composition of the dialysis liquid, and measuring the value of the said characteristic upstream and downstream from the exchanger for each varied composition.

12. The method according to claim 8, further comprising varying a composition of the dialysis liquid, and measuring the value of the said characteristic upstream and downstream from the exchanger for each varied composition.

13. The method according to claim 1, wherein the step of measuring includes measuring a conductivity of the dialysis liquid.

14. The method according to claim 8, wherein the step of measuring includes measuring a conductivity of the dialysis liquid.

15. The method according to claim 9, wherein the step of measuring includes measuring a conductivity of the dialysis liquid.

16. The method according to claim 1, wherein the reference liquid is a sterile physiological serum solution.

17. The method according to claim 8, wherein the reference liquid is a sterile physiological serum solution.

18. The method according to claim 9, wherein the reference liquid is a sterile physiological serum solution.

19. The method according to claim 1, further comprising beginning the step of circulating a non-corporeal reference liquid when the exchanger is in a rinsing and priming stage.

20. The method according to claim 8, further comprising beginning the step of circulating a non-corporeal reference liquid when the exchanger is in a rinsing and priming stage.

21. The method according to claim 9, further comprising beginning the step of circulating a non-corporeal reference liquid when the exchanger is in a rinsing and priming stage.

* * * * *